July 7, 1964 C. FISCHER Plant Pat. 2,417
GLADIOLUS PLANT
Filed May 23, 1963
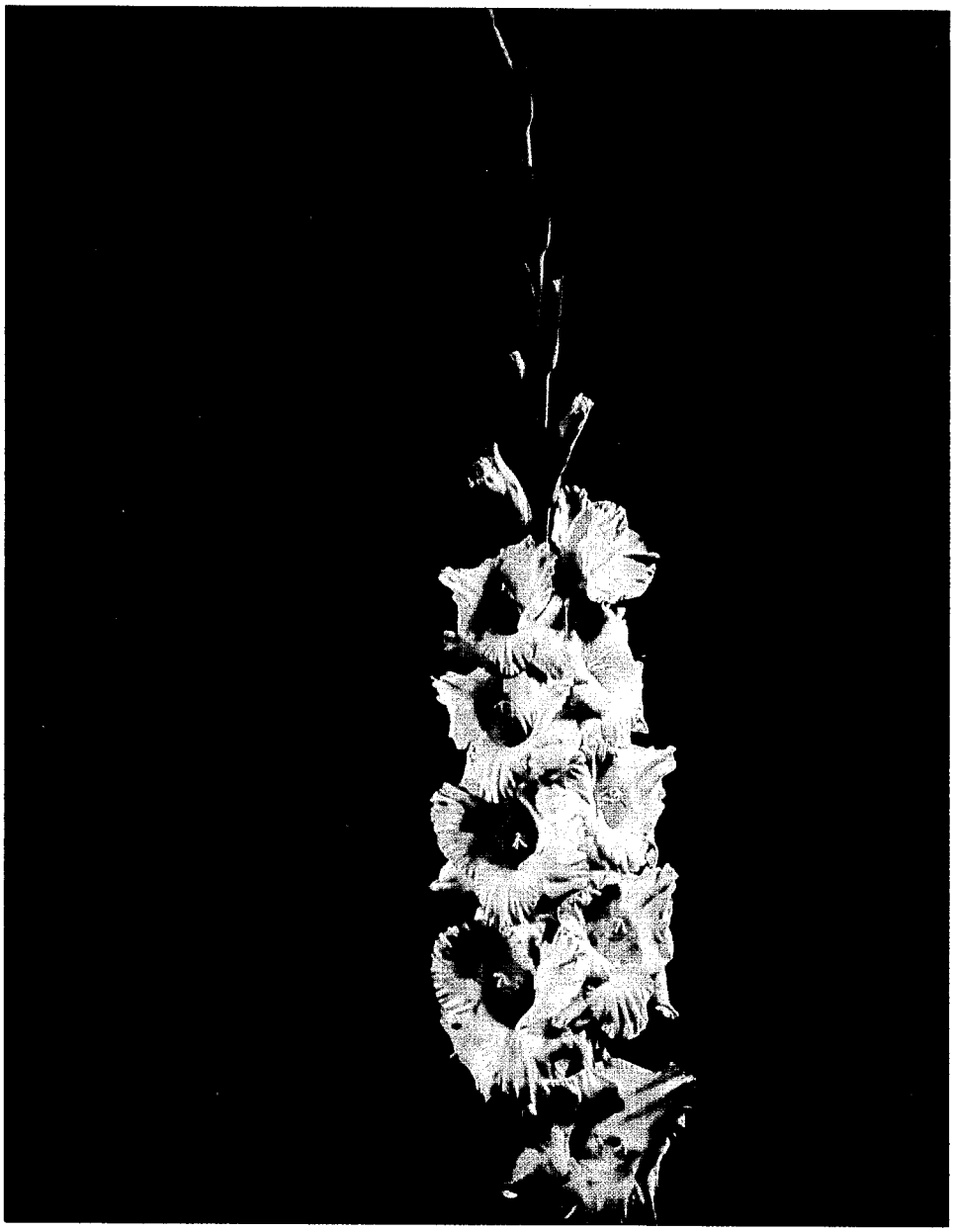
Inventor.
Carl Fischer
By: Robb & Robb
Attorneys.

United States Patent Office

Plant Pat. 2,417
Patented July 7, 1964

2,417
GLADIOLUS PLANT

Carl Fischer, St. Charles, Minn., assignor to Imperial Flowers Limited, Leamington, Ontario, Canada, a corporation of Canada Filed May 23, 1963, Ser. No. 282,825
1 Claim. (Cl. Plt.—85)

The present invention relates to a new and distinct variety of gladiolus plant which was originated by me by crossing the variety "Campanile" (unpatented) with the variety "Innocence" (unpatented), the former being the seed parent, and the latter being the pollen parent.

The primary objective of this breeding was to produce a new and improved gladiolus variety characterized by a vigorous habit of growth and an adaptability to both winter and summer climates in the Southern areas of the United States. This objective was fully achieved, along with other desirable improvements, as evidenced by the following unique combination of characteristics which are outstanding therein and which distinguish it from its parents, as well as from all other varieties of which I am aware:

(1) An extremely vigorous plant habit;

(2) The ability of the flowers to open well from tight buds;

(3) An unusually good adaptability to both winter and summer climates and temperatures over a wide range of latitude, and particularly in Southern latitudes of the United States; and (4) A distinctive and attractive Rhodamine Pink general color tonality of the flowers, said color becoming slightly deeper on the lip petals as the flowers age, and the lip petals having a small white blotch, with the reverse of the florets having a streak of Amaranth Rose radiating outwardly from the calyx.

My new variety resembles the parent variety "Innocence" more than any other known variety, but differs therefrom particularly by having a stronger flower stem; a habit of opening better from tight buds; more fully developed buds at the tip of the flower spike; a deeper flower color; and a habit of producing bulblets of smaller size.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations from cormels.

*Plant*

Growth: Extremely vigorous; prolific propagator.

Blooming habit: Comes into bloom from the planting of large bulbs in the Northern latitudes of the United States in about 85 days.

Stems: Long and willowy.

*Diameter at base.*—About ½ inch.

*Color (at base).*—Pink tinted.

Foliage: Slender; drooping; leaves attain height of about 40 inches. Color—deep green.

Disease resistance: Unusually resistant to the common diseases to which gladiolus varieties are subject, as determined by comparison with other varieties grown in my fields near St. Charles, Minnesota.

Corms (bulbs): Rough appearance; under some conditions, the husk does not develop fully and the corm is rather nude, and flesh bruises easily; husks have a purple cast at the top of the corm. Color of flesh—Amber Yellow, Plate 505/1.

*Flower*

Spike: Blossom spike ranges from about 60 inches to 64 inches tall, with flower head ranging from about 24 inches to 26 inches long; bears from 20 to 22 buds, with 8 or 9 buds open at one time.

Bud:

*Size.*—About 2 inches long when opening.

*Opening.*—Opens exceptionally well from tight buds; 5 or 6 buds show color at one time.

Flower:

*Arrangements.*—Florets usually are informally arranged on the stem; occasionally the lower florets bloom around the stem.

*Size.*—Individual florets average about 5 inches in diameter.

*Form.*—Very recurved; round; ruffled; slightly needle-pointed.

*Keeping qualities.*—Keeps well.

Petals:

*Shape.*—Recurved; ruffled; slightly creased or needlepointed along the midrib.

*Size.*—Upper petal—2¼ inches wide. Lip petal—1½ inches wide.

*Aspect.*—Heavy substance.

*Fragrance.*—None.

*Color.*—Basically Rhodamine Pink, Plate 527/3, becoming slightly deeper on lip petals as flowers fade, with lip petals having a small white blotch, and reverse of florets having a streak of Amaranth Rose, Plate 530 radiating outwardly from the calyx.

*Reproductive Organs*

Stamens: Color—white.

Pistils: Color—white.

I claim:

A new and distinct variety of gladiolus plant, substantially as herein shown and described, characterized particularly as to novelty by the unique combination of an extremely vigorous plant habit, the ability to open exceptionally well from tight buds, good adaptability to both summer and winter climates and temperatures over a wide range of latitude, and particularly in the Southern latitudes of the United States, and a distinctive and attractive Rhodamine Pink general color tonality of the flowers, said flower color becoming slightly deeper on the lip petals as the flowers age, and the lip petals having a small white blotch, and the reverse of the florets having a streak of Amaranth Rose radiating outwardly from the calyx.

No references cited.